United States Patent [19]

Levine et al.

[11] Patent Number: 5,723,285
[45] Date of Patent: Mar. 3, 1998

[54] ASSEMBLY FOR DETECTING BLOOD-BORNE PARASITES AND MEASURING BLOOD SAMPLE PARAMETERS IN A CENTRIFUGED SAMPLE OF BLOOD

[76] Inventors: Robert A. Levine, 31 Pilgrim La., Guilford, Conn. 06443; Stephen C. Wardlaw, 191 N. Cove Rd., Old Saybrook, Conn. 06475

[21] Appl. No.: 655,465

[22] Filed: May 30, 1996

[51] Int. Cl.$^6$ .................. G01N 33/53; G01N 33/558
[52] U.S. Cl. .................. 435/4; 422/58; 422/73; 435/287.1; 435/288.1; 435/288.3; 435/810; 435/970; 436/63; 436/66; 436/67; 436/69; 436/70; 436/164; 436/165; 436/514; 436/805; 436/810
[58] Field of Search .................. 422/58, 73; 435/4, 435/287.1, 288.1, 288.3, 810, 970; 436/514, 63, 66, 67, 69, 70, 164, 165, 805, 810

[56] References Cited

U.S. PATENT DOCUMENTS

| 2,973,580 | 3/1961 | Brown | 33/125 |
| 5,132,087 | 7/1992 | Manion et al. | 422/58 |

*Primary Examiner*—Christopher L. Chin
*Attorney, Agent, or Firm*—William W. Jones

[57] ABSTRACT

Centrifuged anticoagulated blood samples are analyzed under magnification in a centrifuge tube containing a layer-elongating insert, which tube is placed on a calibrated slide. The slide includes a slot in which the tube is placed. A calibrated scale is disposed adjacent to the slot for use in measuring various blood sample parameters, such as hematocrit, platelet count, and the like. Anemia and/or low platelet counts are indicative of potentially serious complications of malaria. Their detection will prompt a physician to consider the liklihood of serious illness due to malaria. The presence or absence of blood-borne parasites can also be determined using the procedures of this invention. Thus the device allows a blood sample to be analyzed for malarial parasites, and also allows measurement of hematicrit and platelet counts. The scale can be presented in a normal image when a simple lens magnification, such as a magnifying glass, is used to view the tube and slide; and can also be presented in mirror image when compound lens magnification, such as a microscope, is used to view the tube and slide.

14 Claims, 3 Drawing Sheets

ASSEMBLY FOR DETECTING BLOOD-BORNE PARASITES AND MEASURING BLOOD SAMPLE PARAMETERS IN A CENTRIFUGED SAMPLE OF BLOOD

TECHNICAL FIELD

This invention relates to the analysis of centrifuged anticoagulated blood samples which are contained in a centrifuge tube having a blood constituent-elongating insert therein. More particularly, this invention relates to a calibrated slide for holding the tube, which slide includes calibration scales that are used to quantify certain blood sample parameters when the blood sample in the tube is viewed under magnification on the slide.

BACKGROUND ART

U.S. Pat. No. 4,027,660 granted to Stephen C. Wardlaw et al describes a method and paraphernalia for use in measuring differential white cell and platelet counts in a centrifuged sample of anticoagulated whole blood. The procedure described in this patent suggests that a scale be used to measure the length of physically expanded white cell and platelet layers, and that a table be used to convert the measured layer lengths to definitive blood cell and platelet layer counts. U.S. Pat. Nos. 4,156,570 and 4,558,947 granted to Stephen C. Wardlaw disclose instruments which are used to measure cell and platelet counts in centrifugal blood samples contained in the aforesaid tube-insert paraphernalia, which instruments include microprocessor controllers that are programmed to automatically convert measured cell and platelet layer band lengths into cell and platelet counts. U.S. Pat. Nos. 4,259,012 granted to Stephen C. Wardlaw, and 5,132,087 granted to Kristen L. Manion et al describe devices for measuring white cell, platelet and hematocrit counts, which devices do not require conversion tables or microprocessor controllers. U.S. Pat. No. 4,209,226 granted to Stephen C. Wardlaw et al describes an optical viewing instrument which includes a capillary tube and a holder which includes a slot for containing the capillary tube. U.S. Pat. No. 4,190,328 granted to Robert A. Levine et al describes a process for the detection of blood-borne parasites wherein a centrifuge tube with an insert are used to trap blood-borne parasites between the tube and the insert so that the parasites will be visible under magnification through the tube.

The aforesaid group of patents all relate to inventions which utilize a tube and insert combination to either measure blood sample parameters quantitatively; or detect the presence or absence of blood-borne parasites, such as malarial microfilaria, or the like. In the latter case, the blood samples in the tubes are examined under magnification, typically with an epi-illuminating UV or fluorescence microscope such as described in U.S. Pat. Nos. 5,198,927, granted Mar. 30, 1993 to R. R. Rathbone et al; and 5,349,468, granted Sep. 20, 1994 to R. R. Rathbone et al. When the centrifuged blood sample is being analyzed for parasites, there is currently no way to simultaneously measure other blood parameters such as hematocrit, platelet counts, hemoglobin, or the like. The reason for this fact is that the microscope used to view the tubes is not equipped to make any of the other blood parameter measurements. Likewise, the equipment used to measure the blood sample parameters such as hematocrit and/or platelet counts cannot presently be used to detect blood parasites. The reason for this fact is that the instruments which analyze the blood sample in the tubes either spin the tubes so that one cannot detect parasites, or they use photo sensors to analyze the blood cell layers, which photo sensors are not equipped to detect parasites. It would be desirable to have blood analyzing equipment which is capable of both detecting blood parasites and measuring other blood sample parameters from the same sample of centrifuged blood contained in the tube-insert combination. Since both anemia and decreased platelet counts are frequently indicators of possible complications of malaria infection, detection of either of these conditions will prompt the physician to look more aggressively for the presence of malaria. It would be highly desirable to have a method and device for both detecting malarial infection and measuring hematocrit and platelet count.

DISCLOSURE OF THE INVENTION

This invention relates to a blood sample tube and a holder therefor, which can be used with a microscope of the type described above to detect blood-borne parasites, and either a microscope as described above or a simple magnifying glass to measure various blood sample parameters. The tube holder is preferably a transparent slide which is provided with a slot in which the blood sample tube is placed. The slide is also provided with blood parameter measurement scales which allow the visual quantification of the hematocrit, and the platelet count in the centrifuged blood sample. At the same time, the blood sample can be visually analyzed for the presence or absence of blood-borne parasites. The blood sampling tube is provided with a visible target blood sample fill line, and the slide is provided with a correction scale which can be used to correct apparent hematocrit and platelet readings to reflect the extent to which the blood sampling tube has actually been filled. The scale indicia are preferably displayed on the tube-holding slide in normal image print, and also in mirror image print. The mirror image print can be read through a microscope, and the normal image print can be read with a magnifying glass, or without magnification.

It is therefore an object of this invention to provide a blood sampling tube and support slide assembly which can be used with a microscope to visually quantify certain blood constituent parameters.

It is a further object of this invention to provide an assembly of the character described which can be used to visually quantify hematocrit and platelet parameters in a centrifuged blood sample which is being examined for the presence or absence of blood-borne parasites.

It is another object of this invention to provide an assembly of the character described wherein the support slide is provided with visible indicia for quantifying the hematocrit and platelet constituents of the centrifuged blood sample.

These and other objects and advantages of the invention will become more readily apparent from the following detailed description of the invention when taken in conjunction with the accompanying drawings, in which:

BEST MODE FOR CARRYING OUT THE INVENTION

Figure 1:
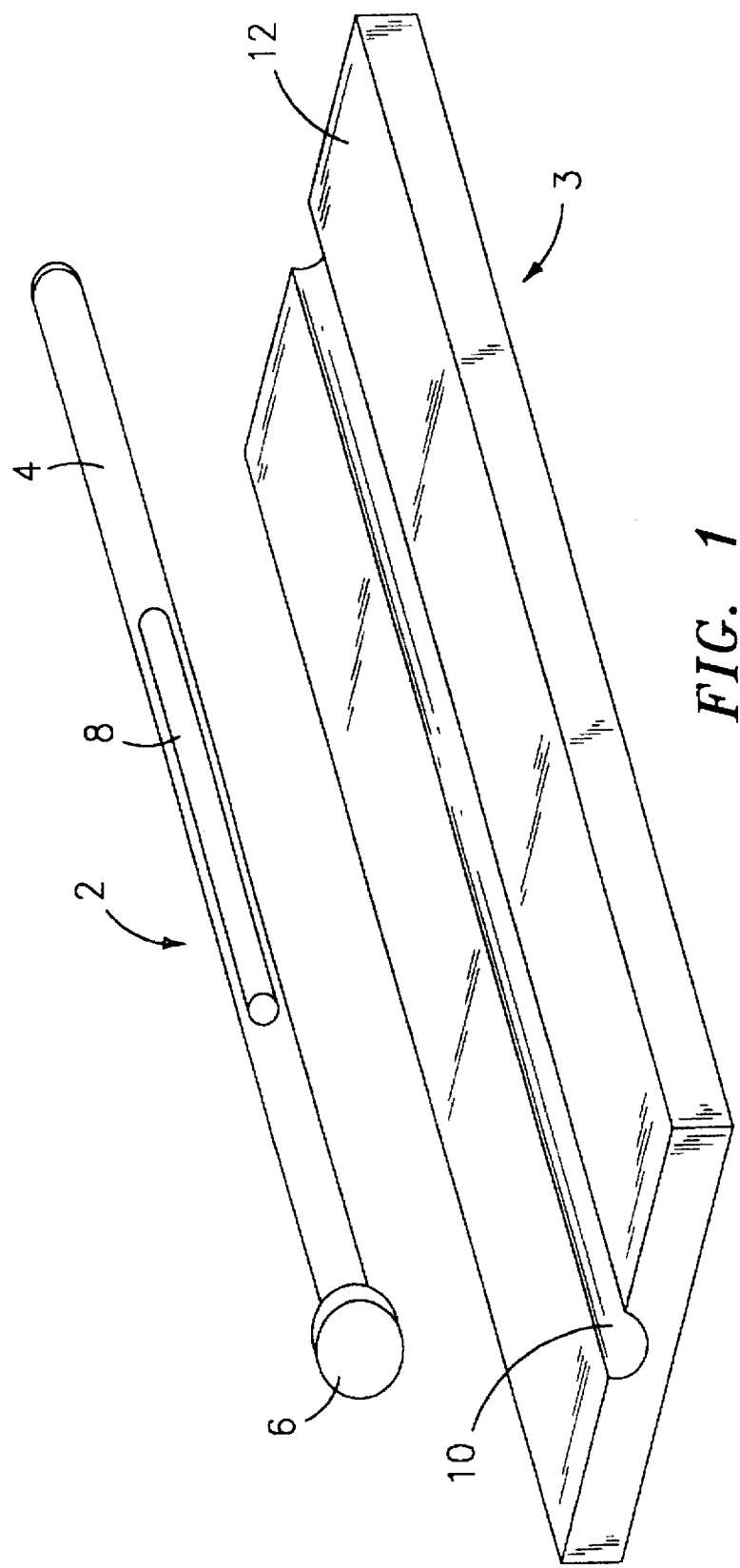
FIG. 1 is an exploded perspective view of a blood sampling tube and tube support assembly which is formed in accordance with this invention.

Referring now to FIG. 1, there is shown a blood sampling tube assemblage denoted generally by the numeral 2, and a tube support slide denoted generally by the numeral 3. The tube assemblage 2 includes a blood sampling tube 4, which may be a capillary tube, or a larger pre-evacuated blood-drawing tube of the type marketed by Becton Dickinson and Company under the trademark VACUTAINER®. When a capillary tube is used, one end of the tube 4 may be closed by a plastic cap 6. The tube 4 contains an elongated, generally cylindrical insert 8 which serves to force any blood-borne parasites outwardly toward the tube bore wall, so that the parasites can be seen under magnification in the blood sample. The tube 4 and insert 8 combination is formed as described in the patents identified first above. The tube 4 will also contain a fluorescent stain that serves to highlight any parasites in the blood sample, and also serves to highlight the platelet layer in the blood sample. Other reagents, such as potassium oxalate, will also be located in the sampling tube 4. The tube support slide 3 includes a slot 10 formed in its upper surface 12, which slot 10 is sized to snugly hold the tube 4.

Figure 2:
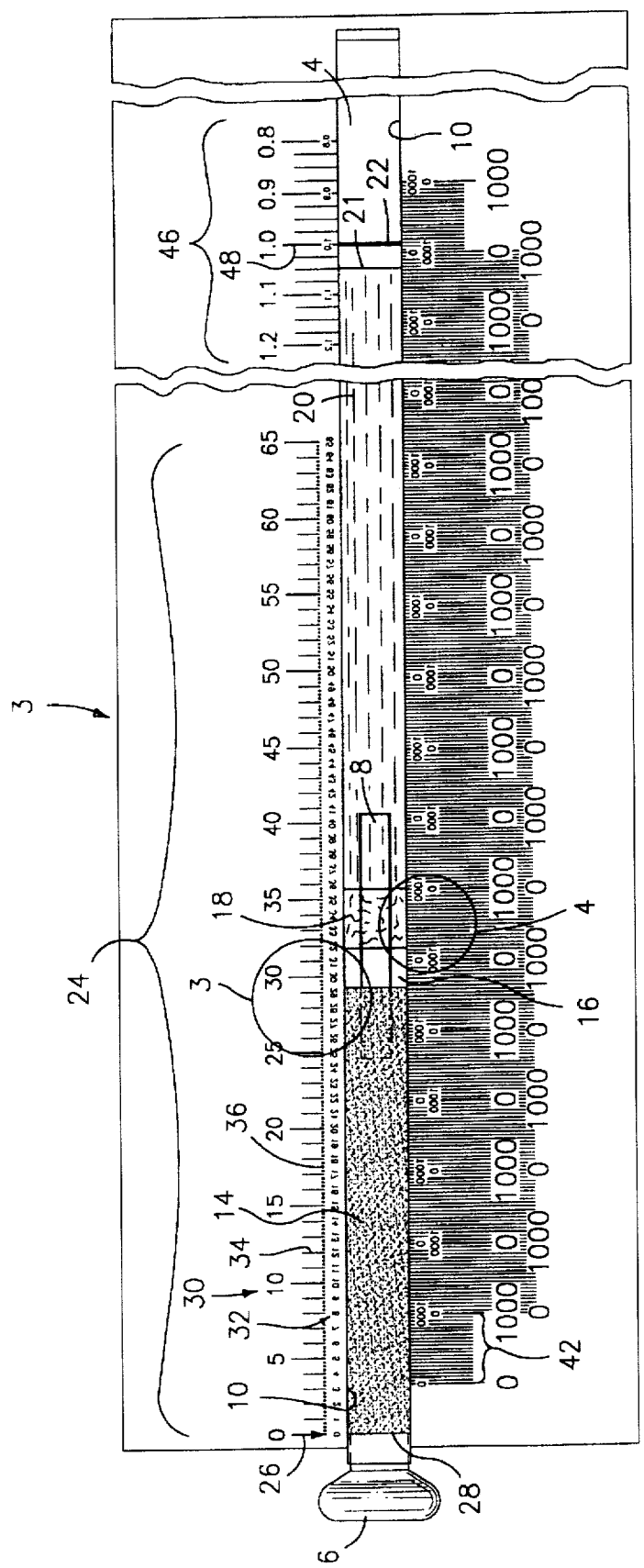
FIG. 2 is a fragmented plan view of the tube and support assembly of this invention showing the blood constituent parameter-measuring indicia on the support.

Opposite sides of the slot 10 have blood constituent parameter scales as shown in FIG. 2. When the anticoagulated whole blood sample is centrifuged in the tube 4, it will gravimetrically separate into several layers which include a red cell layer 14, a white cell layer 16, a platelet layer 18 and a plasma layer 20. The tube 4 is provided with an optimum blood sample fill line 22. When the tube 4 has the optimum amount of blood in it, the upper end 21 of the plasma layer 20 will coincide with the fill line 22 on the tube 4. In the example shown in FIG. 2, the amount of blood in the tube 4 is slightly less than optimum.

The tube holder slide 3 is provided with an hematocrit scale 24 which is used to determine the hematocrit value of the centrifuged blood sample. A "zero" reference line 26 is disposed at one end of the hematocrit scale 24, and the lower end 28 of the red cell layer 14 is aligned with the "zero" line 26 on the slide 3 when the blood sample is analyzed. The hematocrit scale 24 includes two sets of numerical indicia, one set 30 of which is displayed in normal print, and the other set 32 of which is displayed in mirror print. The normal print numerals 30 and their intermediate gradation lines 34 are relatively large and are intended for visualization by the naked eye, or with a relatively low power magnifying glass. The space between each gradation line 34 is divided into quarters by spaced dots 36.

Figure 3:
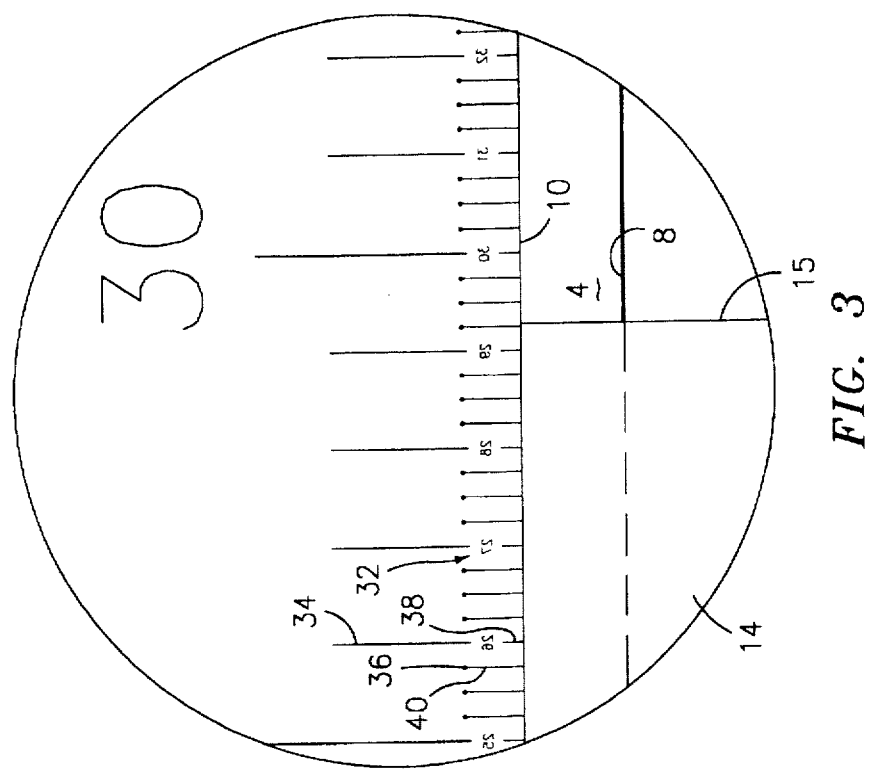
FIG. 3 is an enlarged plan view of detail 3 shown in FIG. 2.

The mirror image numerals 32 are disposed closely adjacent to the slot 10 in which the tube 4 is positioned, and are intended for use with a compound lens viewing device, such as a microscope. It is appreciated that when viewed with such an instrument, the numerals 32 will be reverted so as to be readily legible. As seen in FIG. 3, each of the scale lines 34 and intermediate dots 36 are associated with respective lines 38 and 40 which extend to the edge of the slot 10. The hematocrit reading can thus be determined to within a fraction of one percent of the blood sample. For example, the upper end 15 of the centrifuged red cell layer 14, as shown in FIG. 3, indicates an hematocrit of 29.25 for the blood sample in the tube 4. It will be noted that the hematocrit scale 24 disposed on the slide 3 is adjusted to account for the presence of the insert 8 in the tube 4, and for the fact that the insert 8 will extend into the red cell layer 14; and will also account for any shrinkage of the red blood cells which may be caused by reagents in the tube 4.

Figure 4:
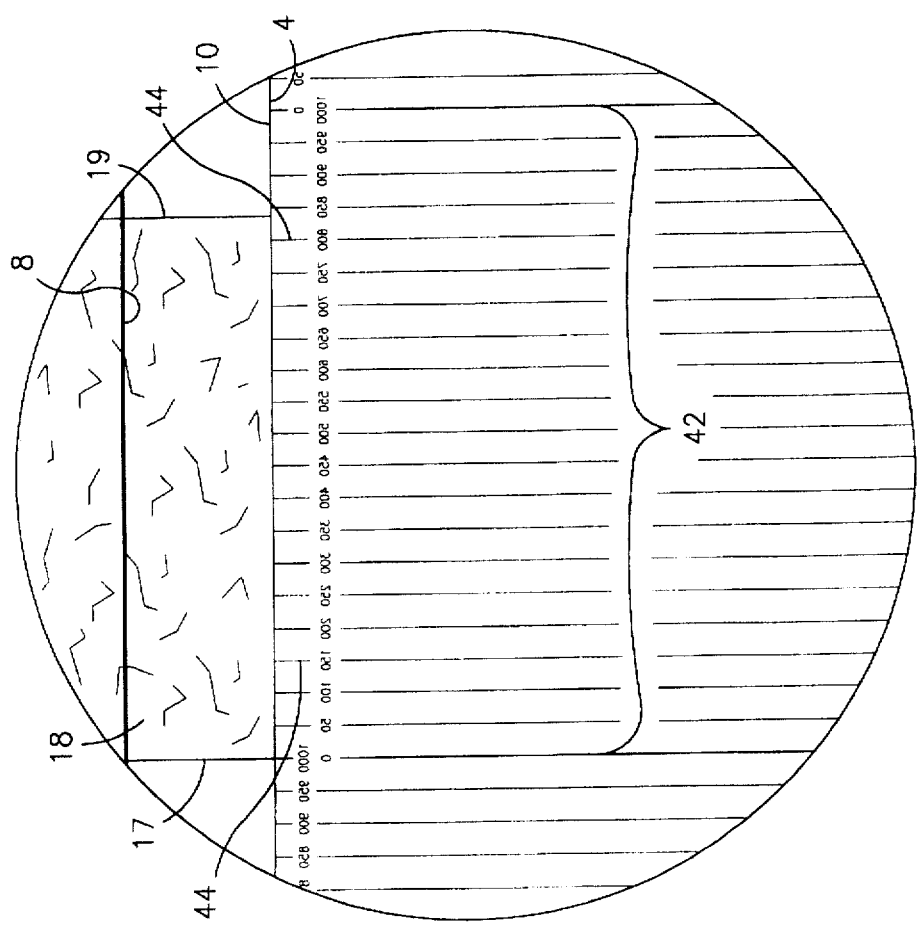
FIG. 4 is an enlarged plan view of detail 4 shown in FIG. 2.

The tube holder slide 3 is also provided with a plurality of platelet count scales 42, each of which is fractionally subdivided as is most clearly shown in FIG. 4. The platelet count scales 42 are divided into equal segments of 50 units extending from 0 to 1,000. It will be noted that there are sets of platelet scales which alternate with each other, so that one scale will be proximal to the slot 10, while the next scale will be distal of the slot 10. Thus the scales 42 alternate, i.e., proximal, distal, proximal, distal, and so forth along the slide 3. The alternating platelet count scales 42 extend along the slide 3 for approximately the same extent as the hematocrit scale 24. The reason for this arrangement is due to the fact that the hematocrit can range from a value of about 8 to a value of above 65. Since the platelet layer 18 will be spaced apart from the upper end 15 of the red cell layer 14, it will be appreciated that the platelet layer 18 can gravitate to any of a number of different locations in the tube 4 after centrifugation of the blood sample. By including a plurality of platelet count scales 42, one need only move the tube 4 axially for a short distance, after determining the hematocrit value, to align the zero line on one of the platelet count scales 42 with the lower end 17 of the platelet layer 18 in the blood sample, as shown in FIG. 4.

As shown in FIG. 4, each 50 unit segment in each platelet scale 42 includes a respective reference line 44 that extends to the edge of the slot 10 so that accurate platelet count readings can be made with the assembly. It will be noted that the platelet count of the centrifuged blood sample shown in FIG. 4 is about $830 \times 10^3/mm^3$. The normal and mirror image printing techniques described above relative to the hematocrit scale are also used on the platelet scales 42, as can be seen in FIGS. 2 and 4.

The slide 3 also includes a blood sample fill correction factor scale 46 (see FIG. 2) which is used to correct the hematocrit and platelet readings to reflect the affect of the total fill level of the blood sample in the tube 4. The correction factor scale 46 is positioned on the slide 12 so that the "1.0" line 48 on the scale 46 will align with the optimum fill line 22 on the tube 4 when the "zero" line 26 is aligned with the lower end 28 of the centrifuged red cell layer 14, and when the tube 4 has been filled to the optimum level. It will be noted in the example illustrated in FIG. 2 that the sample fill level 21 is less than the optimum fill line 22, and that the sample fill level 21 is aligned with the "1.05" line on the correction factor scale 46. Thus the hematocrit and platelet readings will be corrected by multiplying by 1.05.

The assembly of this invention is simple to use. A technician or physician fills the tube 4 with the blood sample, closes the cap 6, and centrifuges the blood sample. The centrifuged sample is then placed in the slot 10 on the tube support slide 3 with the "zero" marker 26 aligned with the lower end 28 of the red cell layer 14. The sample is examined under magnification to determine the presence or absence of blood-borne parasites in the area of the insert 8; the hematocrit reading is made; and the tube 4 is then shifted axially to whatever extent is necessary to align a zero line on one of the platelet scales 42 with the lower end 17 of the platelet layer 18, as shown in FIG. 4, and a platelet count is determined. The volume correction factor is then read and applied. After examining the sample for parasite infesting under higher magnification, the objective lens on the microscope is rotated to produce a lower degree of magnification, on the order of about 2x to 100x, to facilitate reading of the hematocrit and platelet counts.

It will be readily appreciated that the assembly of this invention allows one to visually examine a centrifuged blood sample for the presence or absence of blood-borne parasites, and to measure both hematocrit, and a platelet count in a single sample of centrifuged anticoagulated whole blood. The sampling tube will contain a fluorescent stain such as acridine orange which highlights blood-borne parasites, and which also differentially colors the platelet layer in the blood sample. The assembly can be used with little or no magnification, or can also be used with an appropriately configured microscope to perform the P/A parasite examination, and also to determine the blood constituent parameters.

Since many changes and variations of the disclosed embodiment of the invention may be made without departing from the inventive concept, it is not intended to limit the invention otherwise than as required by the appended claims.

What is claimed is:

1. A slide for holding a centrifuged sample of anticoagulated whole blood contained in a sampling tube, said slide including:

a) a slot for holding the sampling tube;

b) first numerical indicia on the slide adjacent said slot for providing a zero reference baseline on the slide adjacent to one end thereof, said zero reference baseline being positioned on the slide so that one end of a centrifuged red cell pack contained in a sampling tube placed in the slide slot can be aligned with said zero reference baseline;

c) second numerical indicia on the slide adjacent to said slot for providing a hematocrit scale, said hematocrit scale extending from said zero reference baseline and including reference lines extending to an edge of said slot for measuring hematocrit in the centrifuged blood sample in the tube when placed in said slot to an accuracy of at least one percent;

d) third numerical indicia on the slide for providing at least one platelet count scale adjacent to said slot, and on a side of the slot opposite said hematocrit scale, said platelet count scale being operable to measure platelet counts in a centrifuged blood sample in the tube when placed in said slot to an accuracy of at least five percent;

e) fourth numerical indicia on the slide for providing a volume correction factor scale adjacent to said slot, said correction factor scale including multiplication factor reference lines extending to an edge of said slot for alignment with an optimum fill line on a centrifuged blood sample tube placed in the slot, and for concurrent alignment with an actual blood sample fill miniscus in the tube, said multiplication factor reference lines being spaced apart from said zero reference baseline so as to provide correction factors which are operable to correct hematocrit readings and platelet count readings so as to correlate such readings with the actual amount of blood sample in the sample tube; and f) each of said numerical indicia being presented in mirror image on the slide.

2. The slide of claim 1, wherein each of said numerical indicia is present in both conventional and mirror images on the slide.

3. The slide of claim 2 wherein said mirror image numerical indicia are located closer to said slot than said conventional image numerical indicia.

4. The slide of claim 1, wherein said third numerical indicia includes adjacent sequentially repetitive platelet count scales.

5. The slide of claim 4, wherein each of said third numerical indicia in said repetitive platelet count scales is presented in both conventional and mirror images on the slide.

6. The slide of claim 5, wherein said sequentially repetitive platelet count scales include sets of mirror image numerals positioned closely adjacent to said slot and sets of conventional image numerals positioned further away from said slot.

7. The slide of claim 4 wherein each of said sequentially repetitive platelet count scales share a common end line with an adjacent platelet count scale.

8. An assembly for detecting blood borne parasites and measuring centrifuged blood sample parameters in a sample of centrifuged anticoagulated whole blood, said assembly including;

a) a transparent sample tube for containing a sample of centrifuged anticoagulated whole blood, said sampling tube having an optimum sample fill level-indicting indicium, said sample tube containing a generally cylindrical plastic insert having a specific gravity which will cause it to settle into a packed erythrocyte layer in the centrifuged blood sample to force any blood borne parasites in the sample toward a wall of the sample tube and to elongate white cell constituents in the centrifuged blood sample; and b) a slide for holding the sample tube, said slide including:

i) a slot for containing the sample tube;

ii) first numerical indicia on the slide adjacent said slot for providing a zero reference baseline on the slide adjacent to one end thereof, said zero reference baseline being positioned on the slide so that one end of a centrifuged red cell pack contained in the sample tube can be aligned with said zero reference baseline;

iii) second numerical indica on the slide adjacent to said slot for providing a hematocrit scale, said hematocrit scale extending from said zero reference baseline and including reference lines extending to an edge of said slot for measuring hematocrit in a centrifuged blood sample in the sample tube to an accuracy of at least one percent;

iv) third numerical indicia on the slide for providing adjacent sequentially repetitive platelet count scales adjacent to said slot, and on a side of the slot opposite said hematocrit scale, said platelet count scales being operable to measure platelet counts in a centrifuged blood sample in the sample tube to an accuracy of at least five percent; and v) fourth numerical indicia on the slide for providing a volume correction factor scale adjacent to said slot, said correction factor scale including multiplication factor reference lines extending to an edge of said slot for alignment with the optimum fill level-indicating indicium on sampling tube when the latter is placed in the slot, and for concurrent alignment with an actual blood sample fill miniscus in the tube, said multiplication factor reference lines being spaced apart from said zero reference baseline so as to provide a correction factor which is operable to correct hematocrit readings and platelet count readings so as to correlate such readings with the actual amount of blood sample in the sample tube.

9. The assembly of claim 8, wherein each of said numerical indicia is presented in mirror image on the slide.

10. The assembly of claim 9, wherein each of said numerical indicia is present in both conventional and mirror images on the slide.

11. The assembly of claim 10 wherein said mirror image numerical indicia are located closer to said slot than said conventional image numerical indicia.

12. The assembly of claim 8, wherein each of said third numerical indicia in said repetitive platelet count scales is presented in both conventional and mirror images on the slide.

13. The assembly of claim 12, wherein said sequentially repetitive platelet count scales include sets of mirror image numerals positioned closely adjacent to said slot and sets of conventional image numerals positioned further away from said slot.

14. The assembly of claim 8 wherein each of said sequentially repetitive platelet count scales share a common end line with an adjacent platelet count scale.

* * * * *